United States Patent
Hara et al.

(10) Patent No.: US 12,337,111 B2
(45) Date of Patent: Jun. 24, 2025

(54) MASK FOR MECHANICAL VENTILATOR

(71) Applicant: iDevice, Inc., Osaka (JP)

(72) Inventors: Masahiko Hara, Osaka (JP); Yuto Kido, Hirakata (JP); Takashi Kato, Tokyo (JP)

(73) Assignee: IDEVICE, INC., Osaka (JP)

(*) Notice: Subject to any disclaimer, the term of this patent is extended or adjusted under 35 U.S.C. 154(b) by 889 days.

(21) Appl. No.: 17/438,637

(22) PCT Filed: Mar. 3, 2020

(86) PCT No.: PCT/JP2020/008859
§ 371 (c)(1),
(2) Date: Sep. 13, 2021

(87) PCT Pub. No.: WO2020/184280
PCT Pub. Date: Sep. 17, 2020

(65) Prior Publication Data
US 2022/0218931 A1    Jul. 14, 2022

(30) Foreign Application Priority Data

Mar. 11, 2019 (JP) .................................. 2019-044108

(51) Int. Cl.
*A61M 16/06* (2006.01)
(52) U.S. Cl.
CPC .... *A61M 16/0616* (2014.02); *A61M 16/0611* (2014.02); *A61M 2016/0661* (2013.01);
(Continued)
(58) Field of Classification Search
CPC ...... A61M 16/0616; A61M 2016/0661; A61M 16/0683; A61M 2205/02; A61M 16/0611; A61M 16/0605; A61M 16/0622
See application file for complete search history.

(56) References Cited

U.S. PATENT DOCUMENTS

| 2,540,567 A * | 5/1951 | Bennett, V | .......... A62B 18/086 128/206.26 |
| 2,706,983 A * | 4/1955 | Matheson | ............ A62B 18/025 128/206.17 |

(Continued)

FOREIGN PATENT DOCUMENTS

| EP | 2837397 A1 | 2/2015 |
| EP | 2603269 B1 | 2/2018 |

(Continued)

OTHER PUBLICATIONS

International Search Report and Written Opinion with an English translation dated May 19, 2020 for Application No. PCT/JP2020/008859.

(Continued)

*Primary Examiner* — Tu A Vo
(74) *Attorney, Agent, or Firm* — DiPerna Law Firm, P.C.; Raymond A. DiPerna

(57) ABSTRACT

This invention provides a mask for an mechanical ventilator, including a first opening portion that takes in inspired air from the mechanical ventilator, a second opening portion that has an edge abutting against a skin of a user to send the inspired air to at least one of a nose and a mouth of the user, and a bellows portion that is formed on at least a part of the edge of the second opening portion, forms a space for temporarily storing the inspired air and expired air of the user between the first opening portion and the second opening: portion, and deforms following a shape of a face of the user.

15 Claims, 18 Drawing Sheets

(52) U.S. Cl.
CPC ..... *A61M 16/0683* (2013.01); *A61M 2205/02* (2013.01); *A61M 2205/332* (2013.01); *A61M 2205/583* (2013.01); *A61M 2205/584* (2013.01)

(56) References Cited

U.S. PATENT DOCUMENTS

| | | | |
|---|---|---|---|
| 5,074,297 A * | 12/1991 | Venegas | A61M 16/0616 128/205.13 |
| 5,647,345 A | 7/1997 | Saul | |
| 2002/0029780 A1 * | 3/2002 | Frater | A61M 16/0633 128/206.27 |
| 2003/0000001 A1 * | 1/2003 | McDonald | A62B 7/14 2/6.3 |
| 2003/0089372 A1 * | 5/2003 | Frater | A61M 16/0611 128/204.18 |
| 2003/0221691 A1 | 12/2003 | Biener et al. | |
| 2004/0144386 A1 | 7/2004 | Frater et al. | |
| 2004/0182396 A1 * | 9/2004 | Dennis | A62B 18/02 128/205.25 |
| 2007/0000452 A1 | 1/2007 | Barney et al. | |
| 2009/0095301 A1 | 4/2009 | Hitchcock et al. | |
| 2009/0139526 A1 | 6/2009 | Melidis et al. | |
| 2010/0043800 A1 * | 2/2010 | Omura | A61M 16/06 128/207.13 |
| 2012/0055485 A1 * | 3/2012 | Anthony | A61M 16/0611 128/207.18 |
| 2015/0224275 A1 | 8/2015 | Pastoor et al. | |
| 2015/0246199 A1 * | 9/2015 | Matula, Jr. | A61M 16/0622 128/206.24 |
| 2017/0065784 A1 | 3/2017 | Mashal et al. | |
| 2017/0087321 A1 | 3/2017 | Jordan et al. | |
| 2018/0008794 A1 * | 1/2018 | Salmon | A61M 16/0683 |
| 2018/0015241 A1 * | 1/2018 | Jaroslavsky | A61M 15/0088 |
| 2019/0388637 A1 * | 12/2019 | Hitchcock | A61M 16/06 |

FOREIGN PATENT DOCUMENTS

| | | |
|---|---|---|
| JP | 58089018 U | 6/1983 |
| JP | H11397 A | 1/1999 |
| JP | 2008526393 A | 7/2008 |
| JP | 3183049 U | 4/2013 |
| JP | 2013533085 A | 8/2013 |
| JP | 2018102349 A | 7/2018 |

OTHER PUBLICATIONS

Office Action (Notice of Reasons for Refusal) dated Jan. 10, 2023, in Japanese Patent Application No. 2019-182278, with an English machine translation thereof, 10 pages.
Extended European Search Report mailed Nov. 7, 2022 in European Patent Application No. 20769193.2, 14 pages.
First Office Action dated Apr. 15, 2023, in Chinese Patent Application No. 202080019355.9, with an English machine translation thereof, 28 pages.

* cited by examiner

| CONTACT PRESSURE(mmHg) | ① | ② | ③ | ④ | ⑤ | ⑥ | STANDARD DEVIATION |
|---|---|---|---|---|---|---|---|
| EXAMPLE | 4.8 | 7.8 | 4.5 | 8 | 5.4 | 6.5 | 1.5 |
| COMPARATIVE EXAMPLE | 10.5 | 7.7 | 9.7 | 7.3 | 18.4 | 7.7 | 4.2 |

MASK FOR MECHANICAL VENTILATOR

CROSS-REFERENCE TO RELATED APPLICATION

This application is an application under 35 U.S.C. 371 of International Application No. PCT/JP2020/008859 filed on Mar. 3, 2020, which is based upon and claims the benefit of priority from Japanese patent application No. 2019-44108, filed on Mar. 11, 2019, the disclosure of each of which is incorporated herein in its entirety by reference.

TECHNICAL FIELD

The present invention relates to a mask for a mechanical ventilator.

BACKGROUND ART

In the above technical field, patent literature 1 discloses a mask attachment using a bellows configured to reduce an unpleasant feeling when attaching or pain caused by compression.

CITATION LIST

Patent Literature

Patent literature 1: Japanese Patent Laid-Open No. 2018-102349

SUMMARY OF THE INVENTION

Technical Problem

However, in the technique described in the above literature, since the mask cannot sufficiently follow the skin of the user, the attaching feeling is poor.

The present invention enables to provide a technique of solving the above-described problem.

Solution to Problem

One example aspect of the invention provides a mask for an mechanical ventilator, comprising a first opening portion that takes in inspired air from the mechanical ventilator, a second opening portion that has an edge abutting against a skin of a user to send the inspired air to at least one of a nose and a mouth of the user, and a bellows portion that is formed on at least a part of the edge of the second opening portion, forms a space for temporarily storing the inspired air and expired air of the user between the first opening portion and the second opening portion, and deforms following a shape of a face of the user.

Advantageous Effects of Invention

According to the present invention, it is possible to provide a mask for a mechanical ventilator, which has excellent attaching feeling.

DESCRIPTION OF EXAMPLE EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise.

First Example Embodiment

Figure 1:
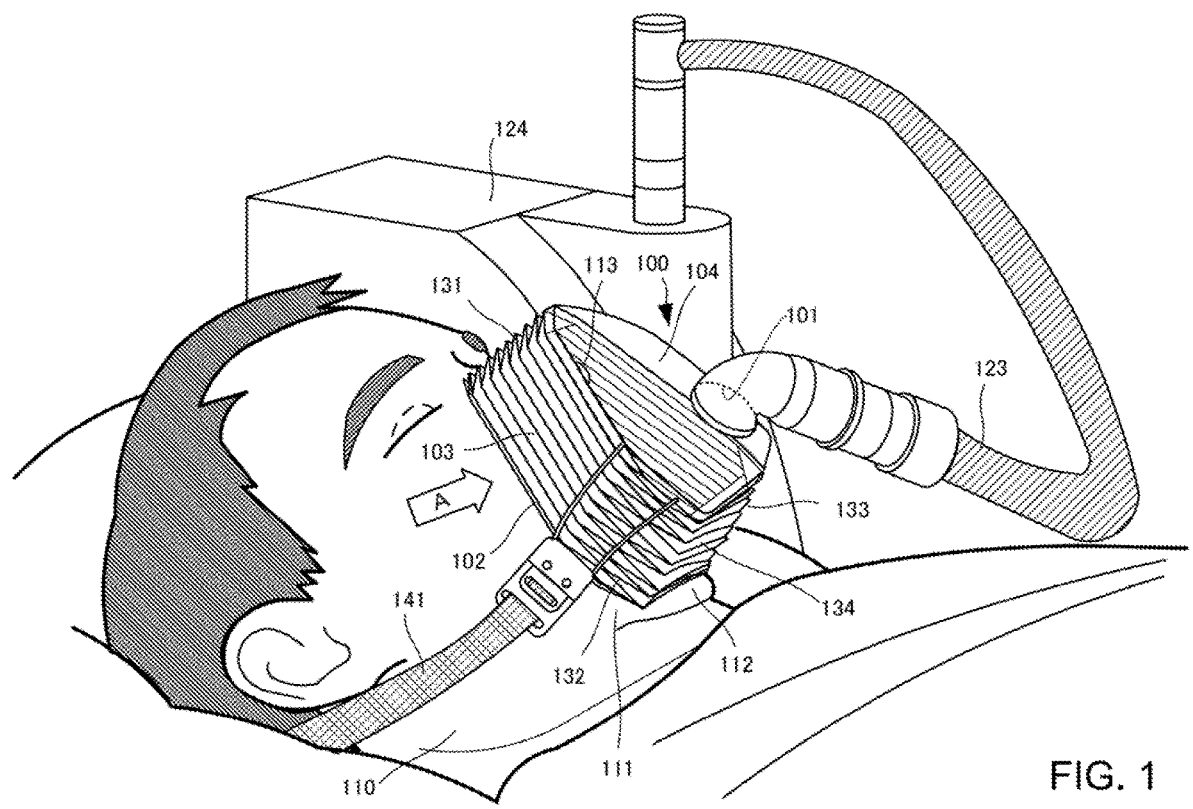
FIG. 1 is a view showing the use state of a mask according to the first example embodiment of the present invention.

A mask 100 for a noninvasive mechanical ventilator according to the first example embodiment of the present invention will be described with reference to FIG. 1. FIG. 1 is a view for explaining the use state of the mask 100.

In general, the object of a mechanical ventilator is to support inspiration, maintain an appropriate ventilation amount of a user, reduce the work of breathing, and improve oxygenation. However since long-time attachment of the mask may cause pressure ulcers in the skin of the user, it is important to control the pressure applied to the skin.

Taking this into consideration, the mask 100 according to this example embodiment includes opening portions 101 and 102, and a bellows portion 103, as shown in FIG. 1.

The opening portion 101 opens to take inspired air from the outside and is connected to a mechanical ventilator 124 via a tube 123 or the like. Here, as the mechanical ventilator 124, a mechanical ventilator for BIPAP (Bilevel Positive Airway Pressure), NIPPV (Noninvasive Positive Pressure Ventilation), or CPAP (Continuous Positive Airway Pressure) is shown. However, the mechanical ventilator according to the present invention is not limited to this and may be a hand pump, and a mask (BVM: Bag Valve Mask) connected to the hand pump and manually held is also included in the concept of the present invention.

A cover 104 provided in a gap between the edge of the periphery of the opening portion 101 and the end portion of the bellows portion is made of a transparent resin and configured such that the user's mouth (for example, the presence/absence to vomiting) can be confirmed even during attachment of the mask 100. However, the present invention is not limited to this, and the cover 104 may be made of an opaque material.

The opening portion 102 is provided Placing the opening portion 101, opens larger than the opening portion 101, and sends the inspired air from the opening portion 101 to at least one of the nose and mouth of a user 110. Here, the opening portion 101 and the opening portion 102 face each other. However, the present invention is not limited to this. The opening portions 101 and 102 may be formed at different angles without facing each other. The opening portion 101 may exist on the chin portion or on a portion between brows and open toward the chin. The opening portion may be provided on a base 134 or near a vertex portion 131 abutting against the nose bridge, or may be provided in the bellows portion 103.

The bellows portion 103 is formed in at least a part of the edge of the opening portion 102, forms a space to temporarily store the inspired air and expired air of the user 110 between the opening portion 101 and the opening portion 102, contacts the skin of the face, and deforms following the shape of the face of the user 110. The bellows portion 103 fits to the skin of the user 110 with a pressure of a predetermined value or less by its cushion property. The bellows portion 103 is preferably made of paper or a composite resin, particularly, silicone. However, the present invention is not limited to this. For example, plastic, rubber, a polymer material, an aluminum sheet, a spring material, or the like may be used. However, the materials are not limited to these, and new materials that implement this function in the future are also included. When viewed from the front of the user 110, the bellows portion 103 includes the vertex portion 131 abutting against the nose root or the nose bridge of the user 110, and vertex portions 132 and 133 abutting against cheeks 111, and has a substantially isosceles triangular shape with a base 134 abutting against a chin 112. Also, the bellows portion 103 has a height of a predetermined value (for example, 5 cm) or more from the cover 104 provided at the edge of the opening portion 101 to the opening portion 102, and has a substantially triangular tubular shape as a whole. A sealed space is formed between the opening portion 101 and the nose and mouth of the user by the bellows portion 103 the cover 104 and the skin of the user 110, and the inspired air from the mechanical ventilator is supplied to the nose or mouth of the user without leaking.

The mask 100 is pressed against the face by a belt 141 wound around the head of the user 110, and the bellows portion 103 is moderately folded upon receiving the pressing force. In other words, the tightening force of the belt 141 is adjusted such that a pressing force that moderately folds the bellows portion 103 with a margin is generated.

Figure 2:
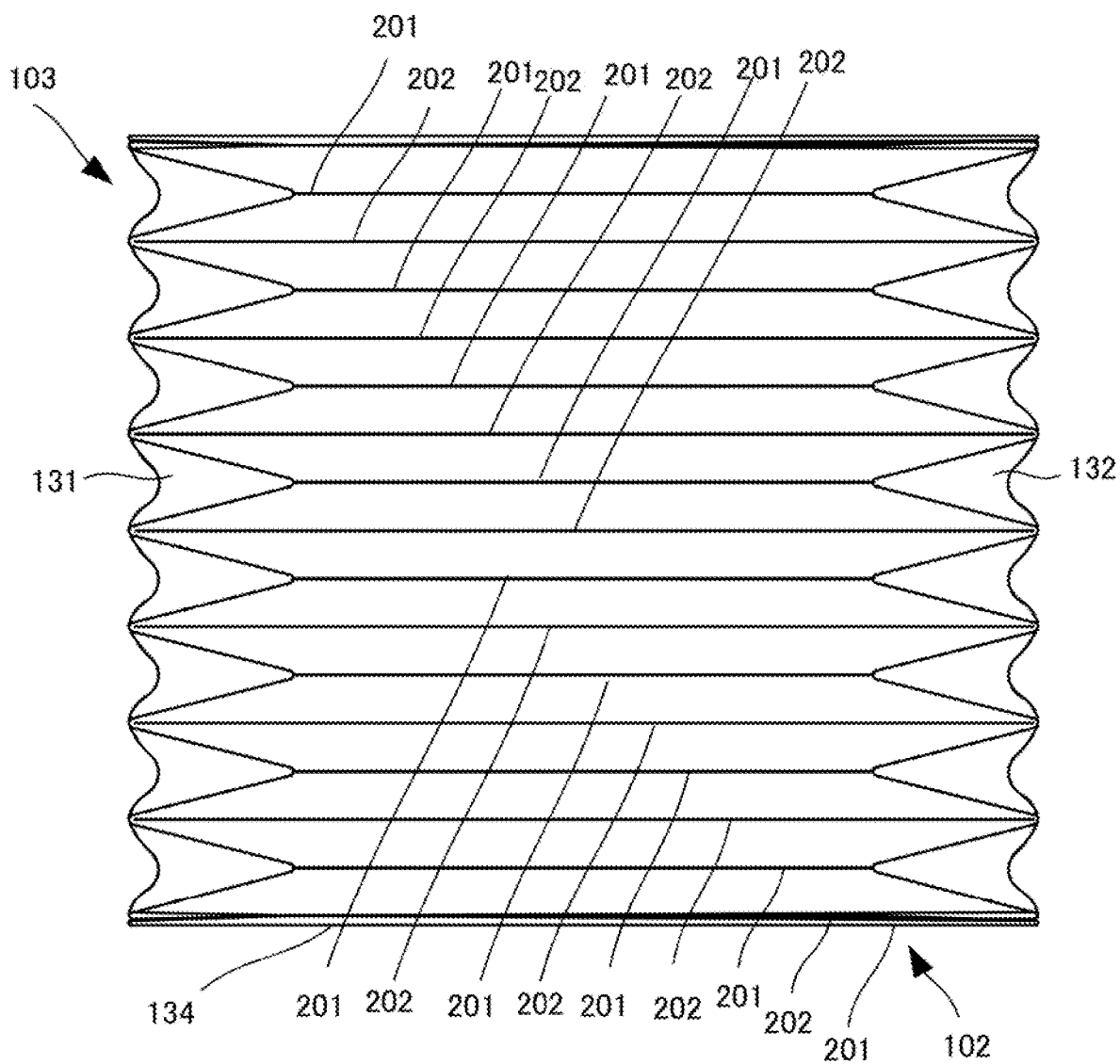
FIG. 2 is a view showing the shape of the bellows portion of the mask according to the first example embodiment of the present invention.
Figure 3:
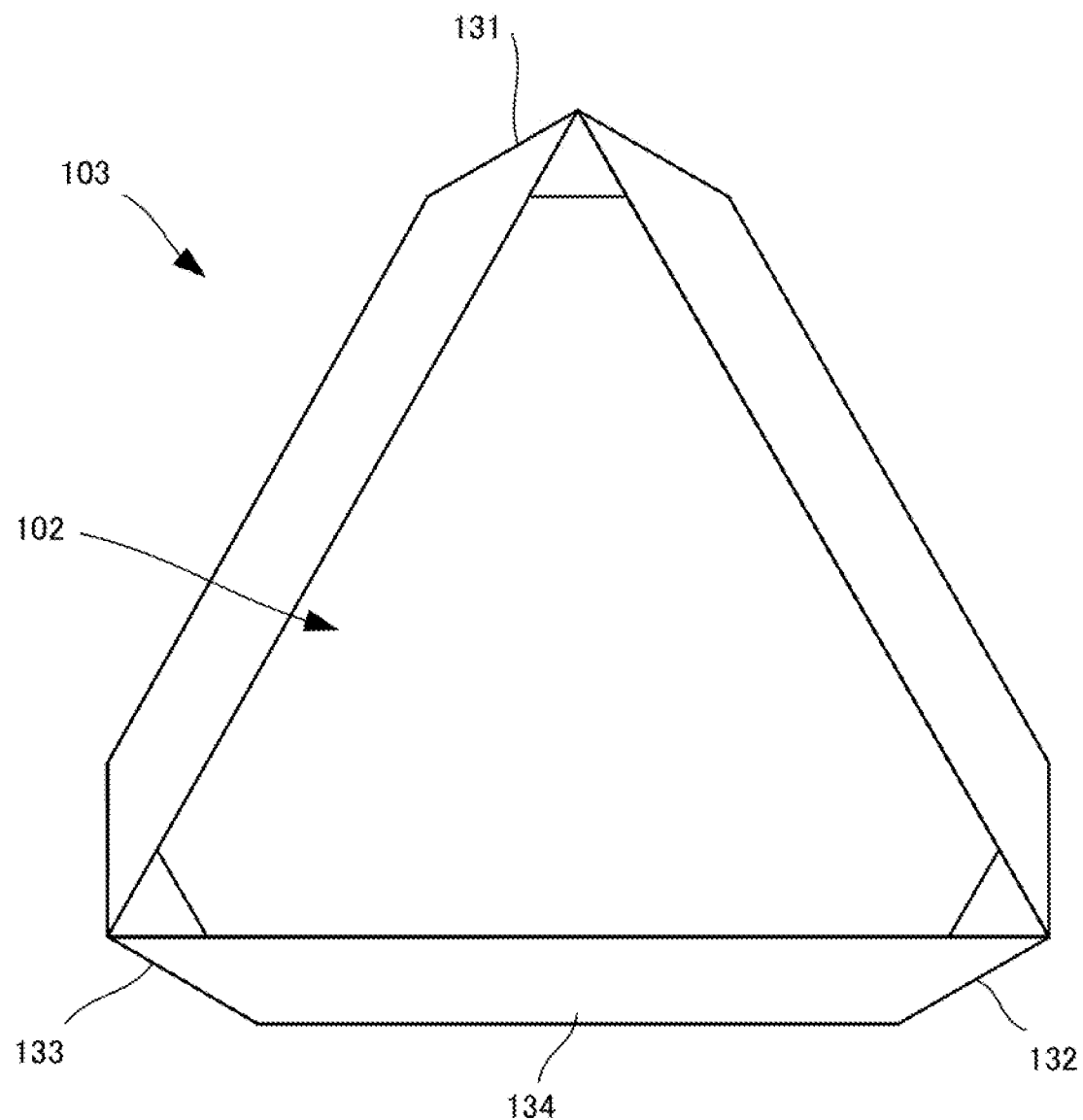
FIG. 3 is a view showing the shape of the bellows portion of the mask according to the first example embodiment of the present invention.

FIGS. 2 and 3 are views for explaining the detailed shape of the bellows portion 103. When viewed from a direction A in FIG. 1, in the bellows portion 103, a plurality of short mountain folds 201 and valley folds 202 longer than the mountain folds 201 are alternately formed, as shown in FIG. 2. The edge closest to the opening portion 102 is preferably the mountain fold 201. When the final surface of the bellows is folded inside, the pressure in the internal space of the bellows portion 103 becomes the force of pressing the final surface downward in FIG. 2. Hence, the contact pressure to the skin of the user 110 becomes higher.

When viewed from the side of the mouth of the user 110 in FIG. 1, the bellows portion 103 has bellows in which the vertex portions 131, 132, and 133 are folded inside, as shown in FIG. 3. As a result, the cross section of the bellows portion 103 in the horizontal direction forms a hexagon.

The bellows portion 103 fits to the nose root or the nose bridge of the user 110 with a pressure of a predetermined value (for example, 15 mmHg) or less by its cushion property, and also fits to the cheeks of the user with a pressure of a predetermined value (for example, 4 mmHg) or less by its restoring force.

On the other hand, if the mask 100 is pressed against the face such that a pressure of the predetermined value or more is applied to the skin of the user 110 by tightening of the belt 141, the bellows portion 103 deforms, and it is therefore difficult to function as a mechanical ventilator. For example, if the bellows portion 103 is excessively folded, a nose tip 113 of the user 110 abuts against the inside of the transparent cover 104 of the opening portion 101, and the user and an operator on the periphery can very clearly know that the belt 141 is tightened too much. Also, since the bellows portion 103 constitutes the most part of the mask 100, medical staff can easily judge, by checking how the bellows portion 103 is folded, that the belt 141 is tightened too much.

Figure 4:
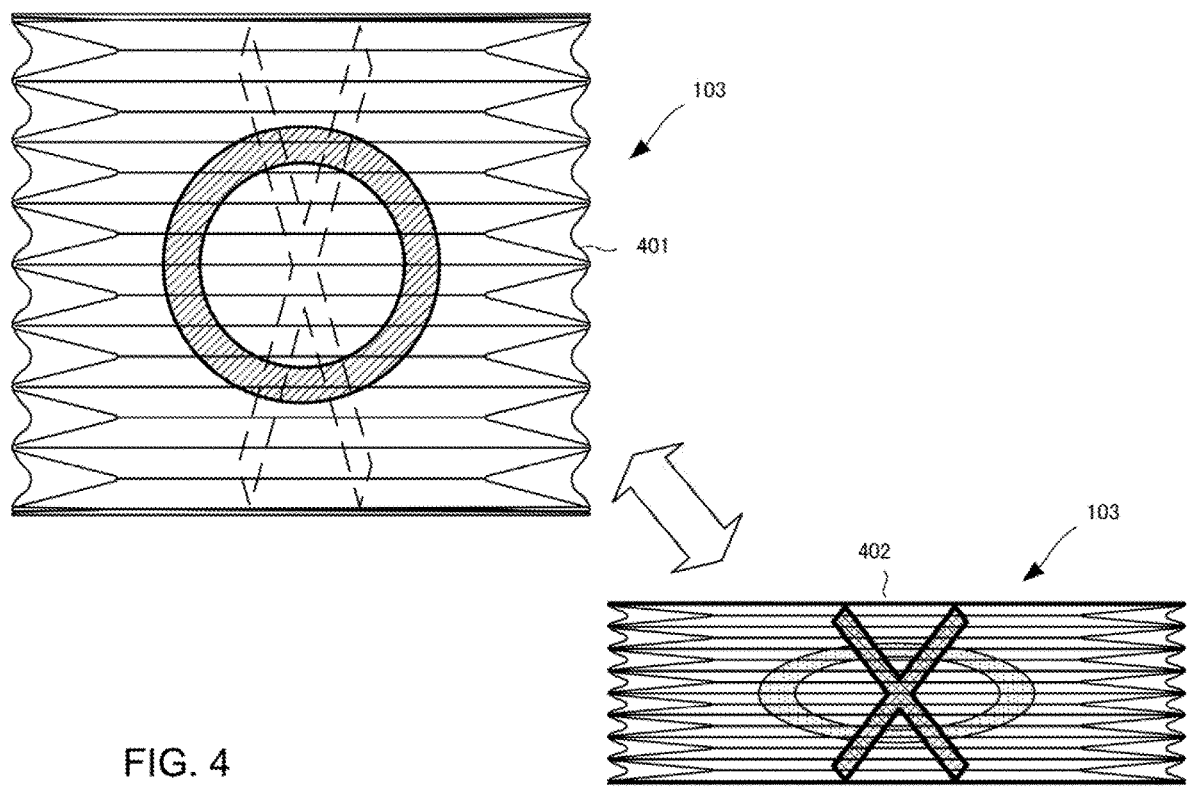
FIG. 4 is a view showing the configuration of the bellows portion of the mask according to the first example embodiment of the present invention.

Also, as shown in FIG. 4, the outer peripheral portion of the bellows portion 103 may be colored such that "○" can clearly be visually recognized in a state 401 in which the bellows portion 103 is expanded without being greatly folded, and "x" can clearly be visually recognized in a state 402 in which the bellows portion 103 is largely folded and contracted to a predetermined value or less. For example, when coloring of elements that form the "x" is not performed in the valley folds, "x" looks light in the expanded state, and "x" looks dark and clear in the contracted state. An example in which symbols such as "○" and "x" are drawn has been described here. However, the present invention is not limited to this, and contact pressures (the unit if mmHg) such as "5" and "10" may be written, or characters such as "tightened too much" may be visible. Also, as these notifications, information obtained from, for example, an electronic pressure sensor may be transmitted to an electronic device by Bluetooth®. As described above, since it is possible to clearly notify that the belt 141 is tightened too much, pressure ulcers in the skin of the user can be prevented.

According to the above-described configuration, the bellows portion 103 having elasticity deforms following the shape of the face of the user. Hence, since the mask 100 tightly contacts skin of the user 110 with such a moderate pressure that presses skin not too much and does not cause leakage of inspired air, the attaching feeling, for the user 110 can be improved.

Note that m this example embodiment, the bellows portion is formed on the entire edge of the opening portion 102. However, the present invention is not limited to this. The bellows portion need only be formed on a part of the edge of the opening portion 102, more specifically, on one of die nose root portion, the nose bridge portion, the cheek portion, and the lower jaw portion or a combination thereof. Also, a sheet-shaped cushion material may be provided on a surface of the bellows portion, which comes into contact with the skin of the user.

Second Example Embodiment

Figure 5:
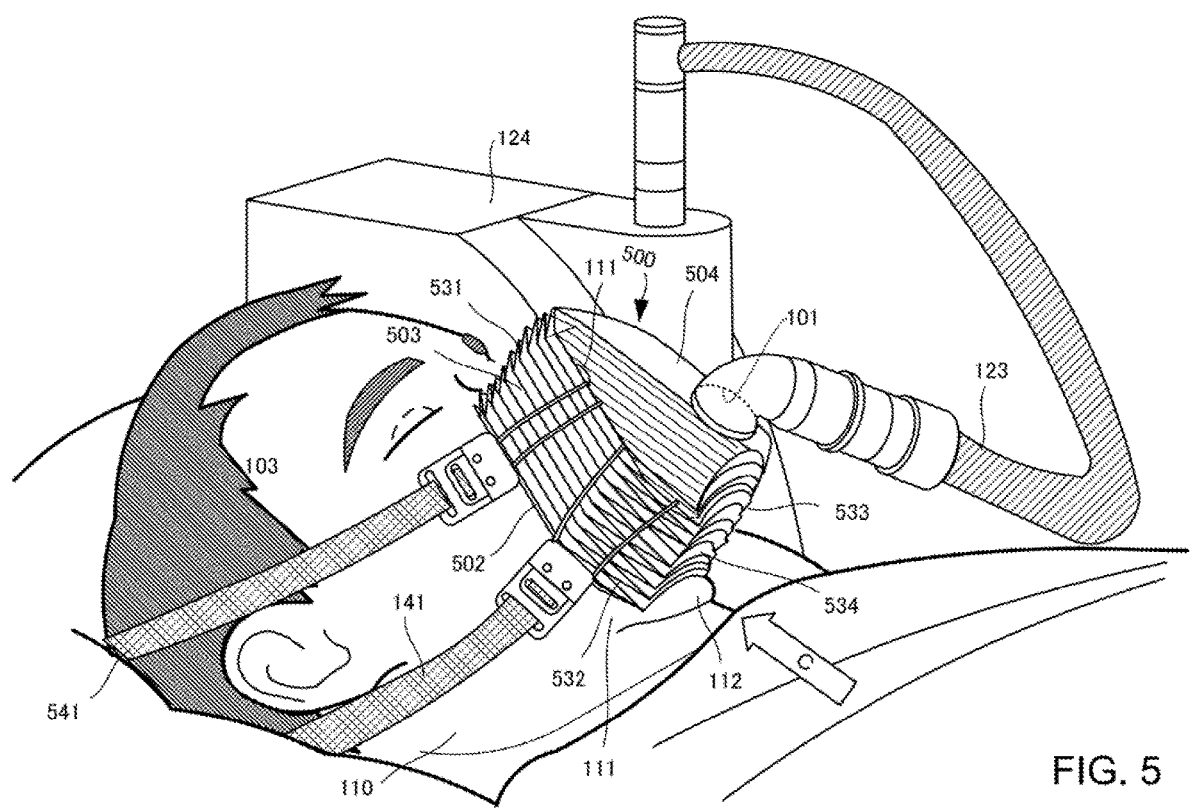
FIG. 5 is a view showing the use state of a mask according to the second example embodiment of the present invention.

A mask 500 according to the second example embodiment of the present invention will be described next with reference to FIG. 5. FIG. 5 is a view for explaining the use state of the mask 500. The mask 500 according to this example embodiment is different from the above-described first example embodiment in that a bellows portion 503 has a taper such that its cross section in the horizontal direction becomes narrow from the side of an opening portion 101 to the side of an opening portion 502, in the configuration of a cover 504, and in that a belt 541 is provided on both sides of the nose. The rest of the components and operations is the same as in the first example embodiment. Hence, the same reference numerals denote the same components and operations, and a detailed description thereof will be omitted.

The bellows portion 503 includes a vertex portion 531 abutting against the nose root or the nose bridge of a user 110, and vertex portions 532 and 533 abutting against cheeks of the user 110, and has a substantially isosceles triangular shape with a base 534 abutting against a chin 112 of the user 110, as in FIG. 1. The cover 504 on the periphery of the opening portion 101 is made of a transparent resin, and deforms by the tensile force of the belts 141 and 541.

Figure 6:
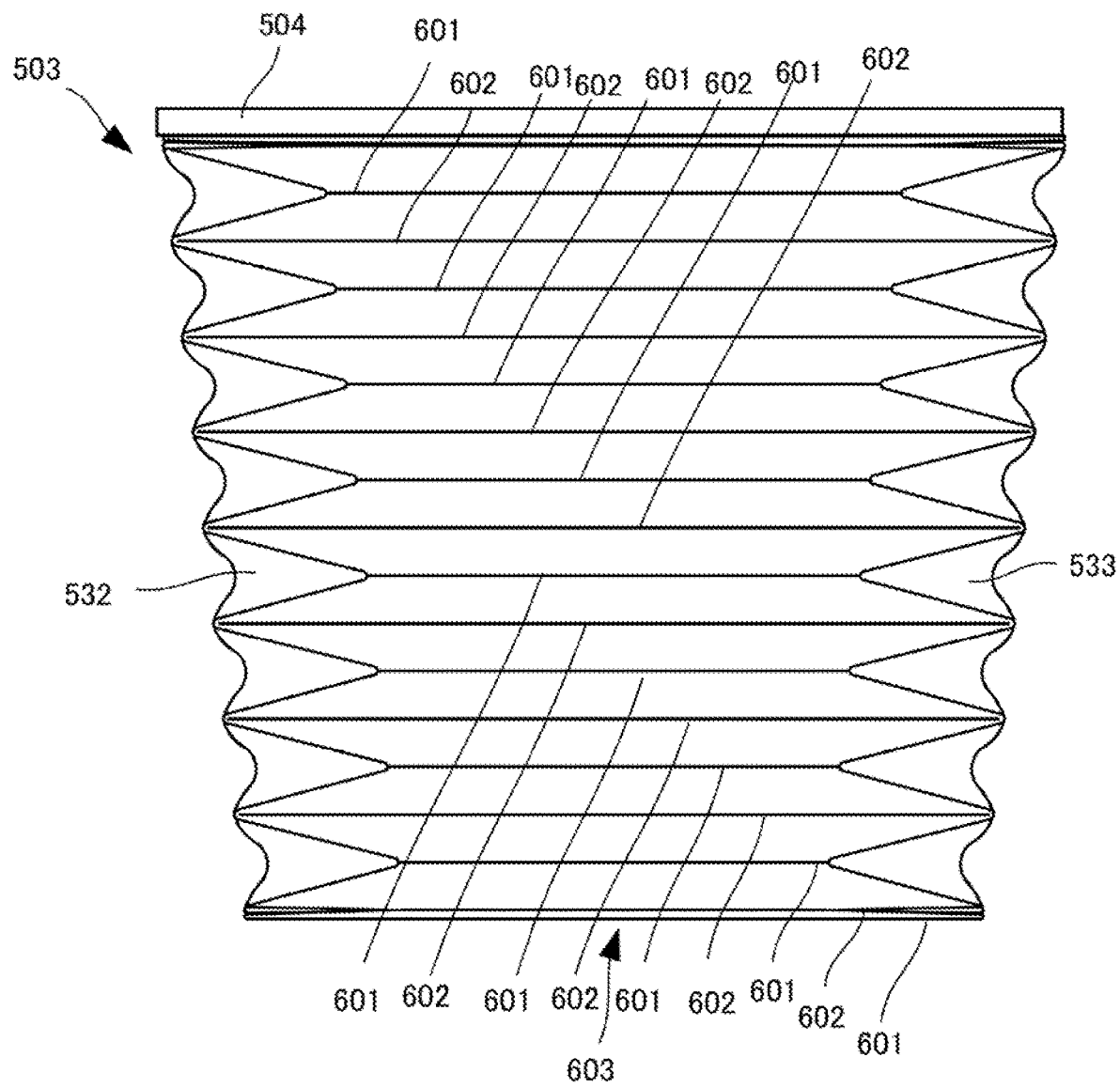
FIG. 6 is a view showing the shape of the bellows portion of the mask according to the second example embodiment of the present invention.
Figure 7:
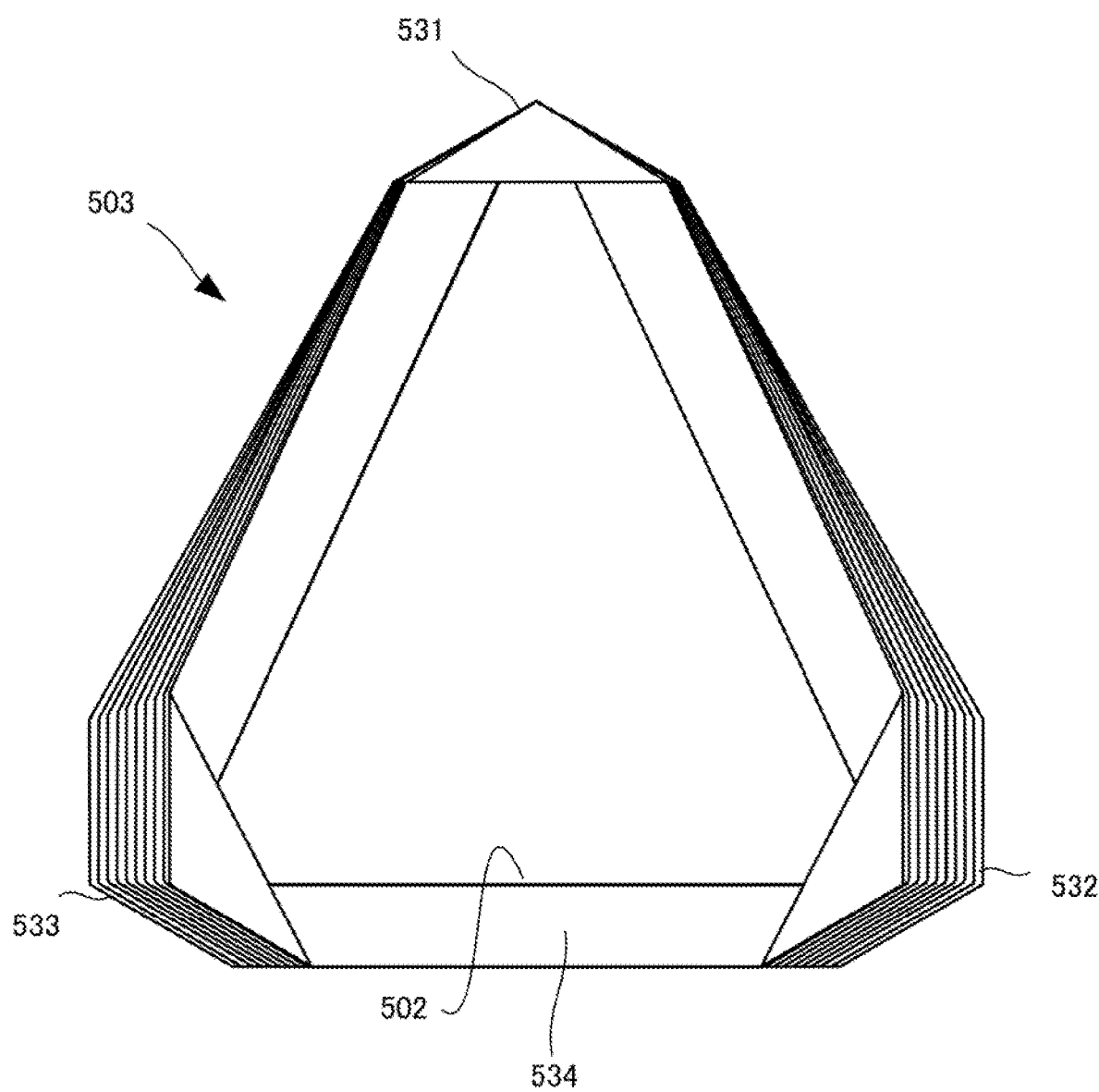
FIG. 7 is a view showing the shape of the bellows portion of the mask according to the second example embodiment of the present invention.
Figure 8:
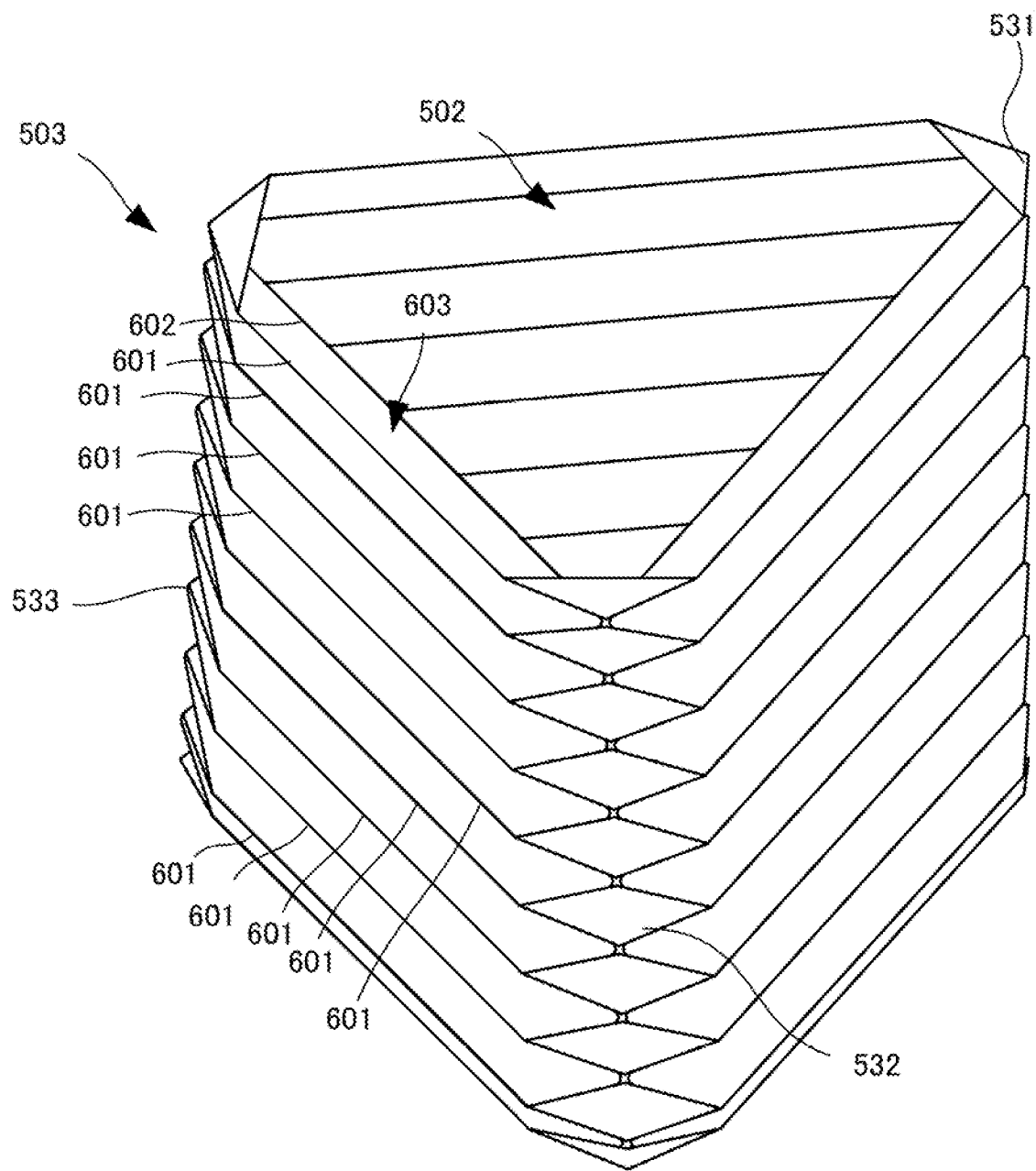
FIG. 8 is a view showing the shape of the bellows portion of the mask according to the second example embodiment of the present invention.

FIGS. 6 to 8 are views for explaining the shape of the bellows portion 503 before attachment. When viewed from a direction C in FIG. 5, in the bellows portion 503, a plurality of short mountain folds 601 and valley folds 602 longer than the mountain folds 601 are alternately formed, as shown in FIG. 6. In an unattached state, as shown in FIG. 6, the bellows portion 503 has a side surface in a substantially isosceles trapezoid shape, and the cover 504 has a flat plate shape. However, the cover 504 is not limited to this, and a shape and a material which enable elastic deformation by the tensile force of the belts 141 and 541 suffice.

Because of the taper, the bellows portion 503 easily bends to both the left and right sides with respect to an abutting, position 603 to the chin located on the midline of a human as the center in an attached state, and the adhesion to the cheeks increases.

When viewed from the side of the mouth of the user 110 in FIG. 5, the bellows portion 503 has a bellows in which the distance between the vertex portions 532 and 533 gradually becomes narrow, as shown in FIG. 7. As a result, the bellows portion 503 has a taper that is formed such that the cross section in the horizontal direction becomes narrow toward the side of the mouth of the user 110. FIG. 8 is a perspective view of the bellows portion 503. FIG. 8 shows a perspective view viewed from the side of the opening portion 502 to facilitate understanding. When the bellows portion 503 bends with respect to the abutting position 603 to the chin as the center, the vertex portions 532 and 533 readily come into tight contact with the cheeks of the user 110.

Figure 9:
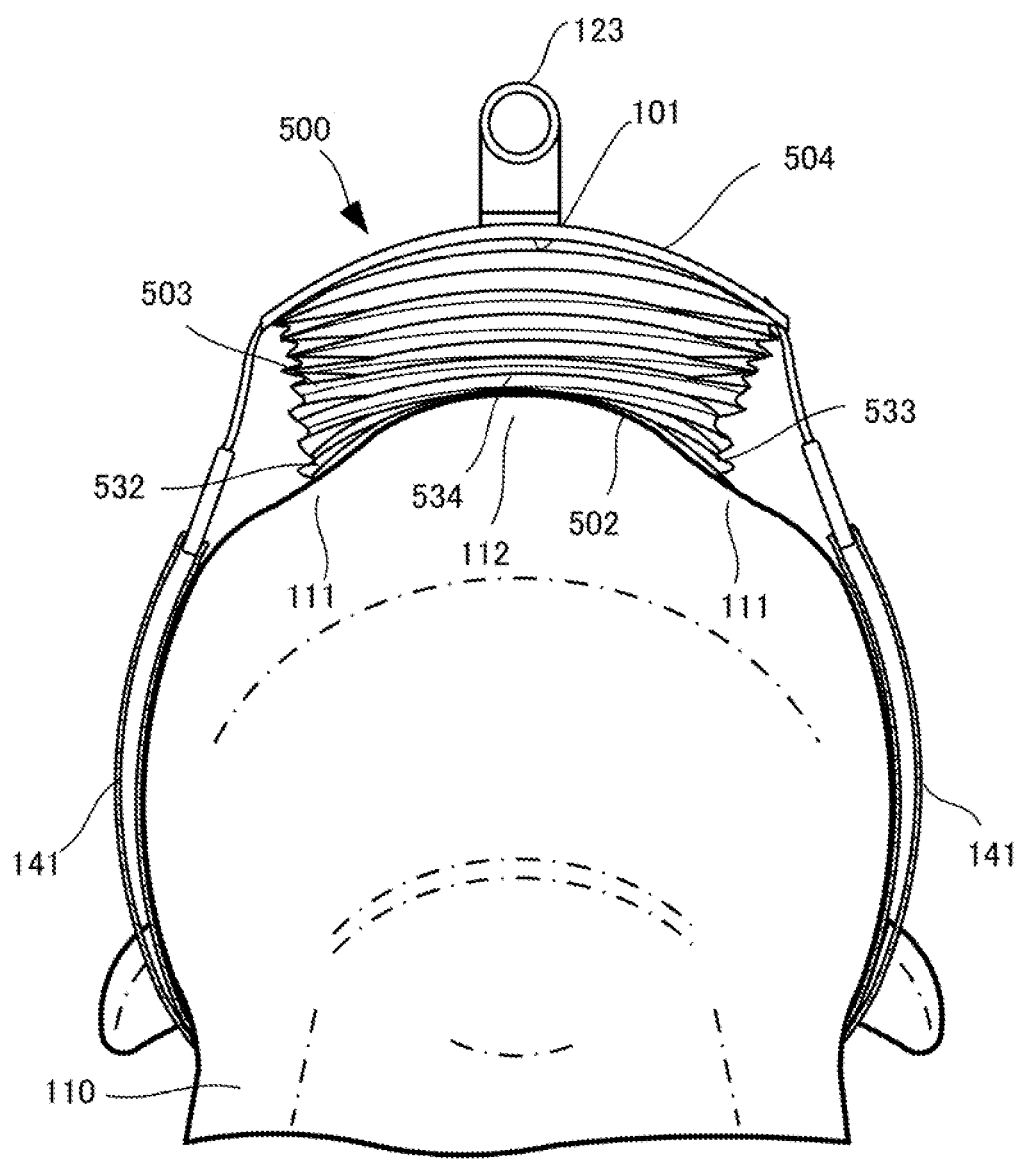
FIG. 9 is a view showing the use state of the mask according to the second example embodiment of the present invention.

FIG. 9 is a view showing the use state of the mask 500 when viewed, from the lower side (the direction C in FIG. 5) of the chin 112 of the user 110. As shown in FIG. 9, the base 534 of the bellows portion 503 abuts against the chin 112 and bends. Also, in FIG. 9, the cover 504 on the upper side of the bellows portion 503 also deforms into an arc shape projecting upward due to the tensile force of the belts 141 and 541. Accordingly, the vertex portions 532 and 533 come into tight contact with the cheeks of the user 110, and airtightness in the mask 500 improves. This is expected to have a great effect for a user with hollow cheeks.

As described above, according to this example embodiment, in addition to the first example embodiment, it is possible to improve the adhesion to the skin without losing the attaching feeling for the user, and also improve the airtightness of the mask 500 and maintain an appropriate ventilation amount of the user.

Third Example Embodiment

Figure 10:
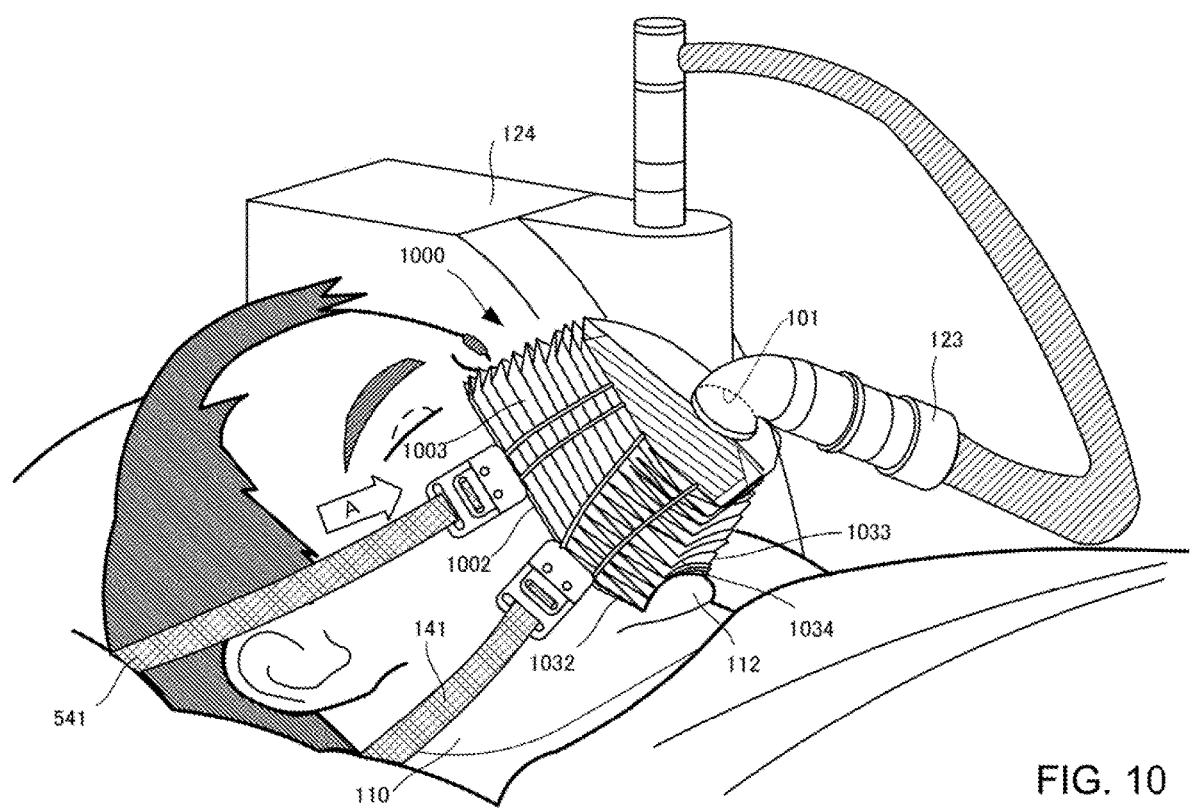
FIG. 10 is a view showing the use state of a mask according to the third example embodiment of the present invention.

A mask 1000 according to the third example embodiment of the present invention will be described next with reference to FIG. 10. FIG. 10 is a perspective view for explaining the use state of the mask 1000. The mask 1000 according to this example embodiment is different from the above-described second example embodiment in that a taper is provided such that the cross section of a bellows portion 1003 in the horizontal direction becomes wide from the side of an opening portion 101 to the side of an opening portion 1002. The rest of the components and operations is the same as in the second example embodiment. Hence, the same reference numerals denote the same components and operations, and a detailed description thereof will be omitted.

Figure 11:
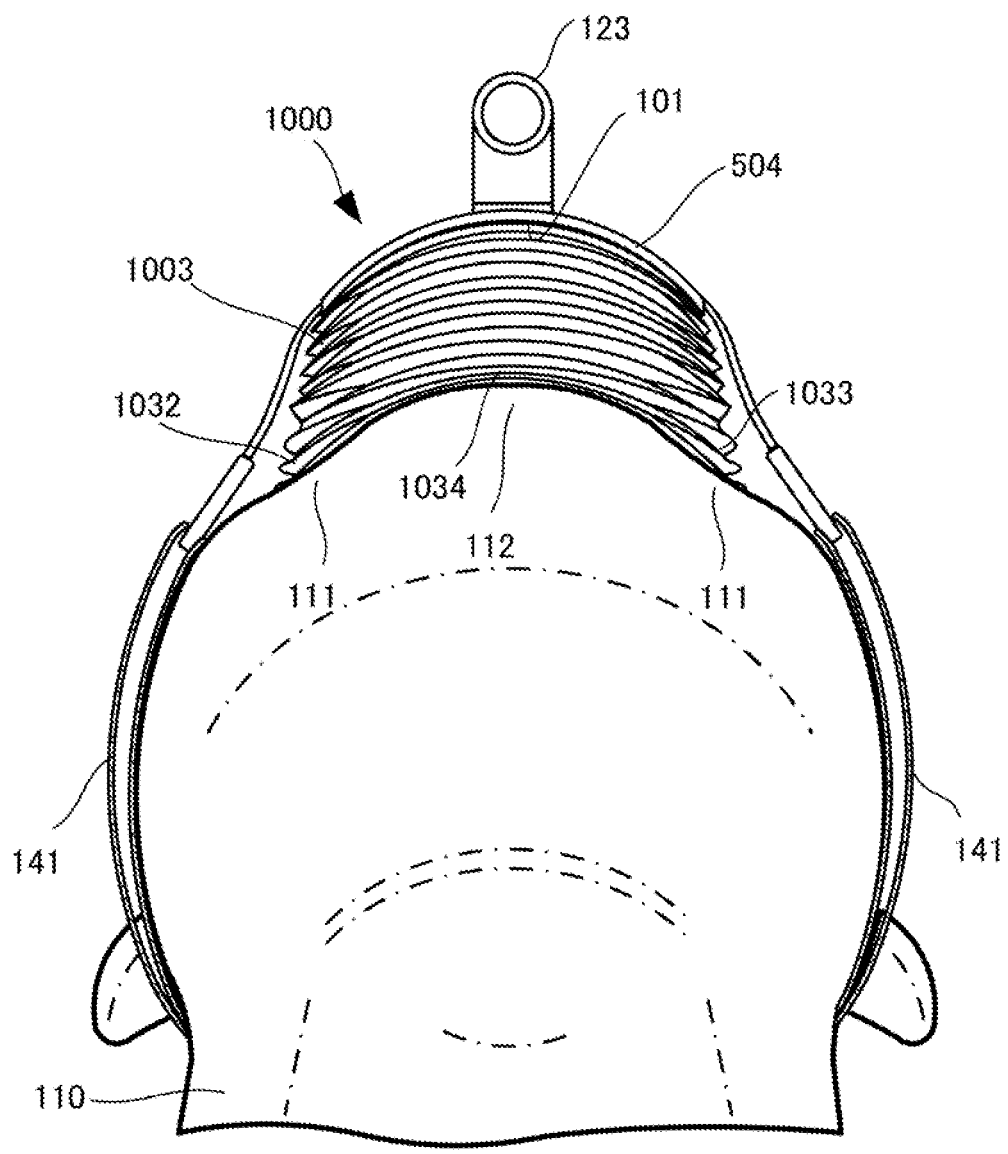
FIG. 11 is a view showing the use state of the mask according to the third example embodiment of the present invention.

FIG. 11 is a view showing the use state of the mask 1000 when viewed from the lower side of a chin 112 of a user 110. As shown in FIG. 11, a base 1034 of the bellows portion 1003 abuts against the chin 112 and bends. Accordingly, vertex portions 1032 and 1033 come into tight contact with cheeks 111 of the user 110, and airtightness in the mask 1000 improves. This is expected to have a great effect for a user with bulging cheeks.

Fourth Example Embodiment

Figure 12:
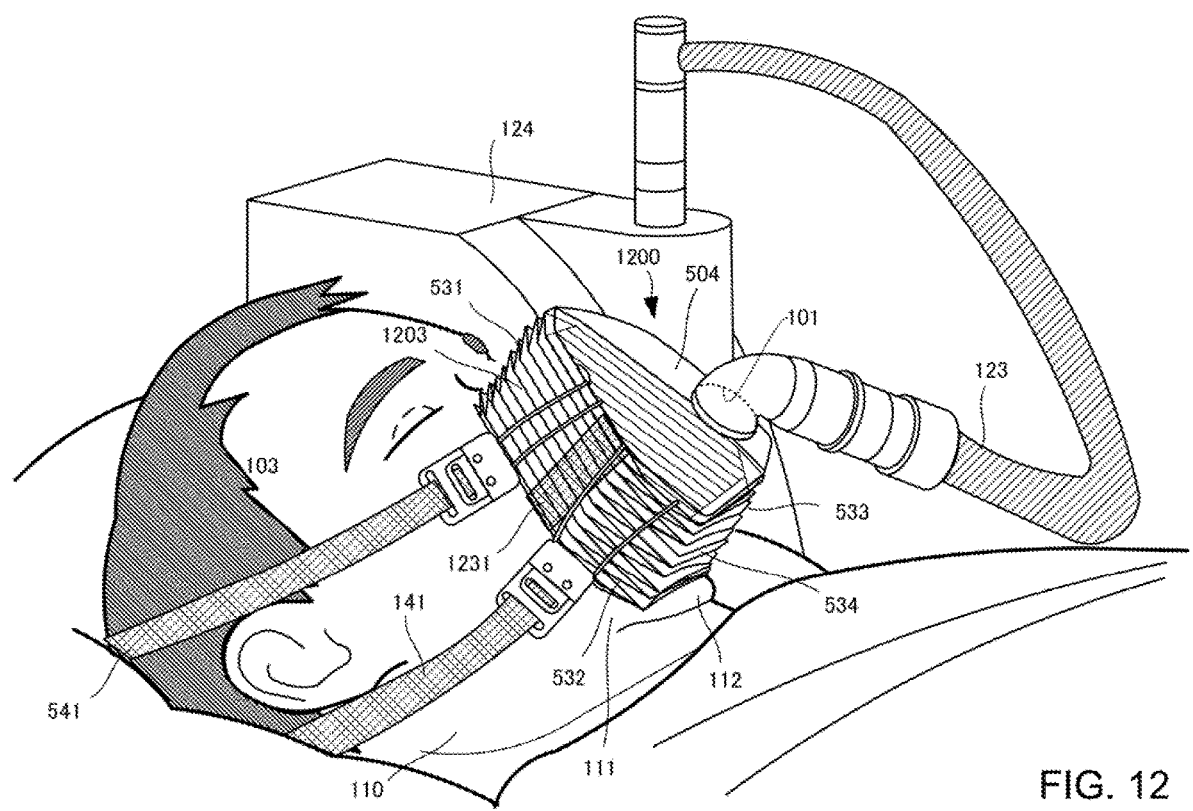
FIG. 12 is a view showing the use state of a mask according to the fourth example embodiment of the present invention.

A mask 1200 according to the fourth example embodiment of the present invention will be described next with reference to FIG. 12. FIG. 12 is a view for explaining the use slate of die mask 1200. The mask 1200 according to this example embodiment is different from the above-described second example embodiment in that a reinforcing member 1231 is provided on each of a surface between a vertex portion 531 and a vertex portion 532 of a bellows portion 1203 and a surface between the vertex portion 531 and a vertex portion 533. The rest of the components and operations is the same as in the second example embodiment. Hence, the same reference numerals denote the same components and operations, and a detailed description thereof will be omitted.

When the reinforcing members 1231 are provided, the elastic force (the repelling force or the force of returning to the original state) around the vertex portions 532 and 533 of the bellows portion 1203 increases, and the vertex portions 532 and 533 thus more firmly fit to cheeks 111 (for example, 4 mmHg or more). On the other hand, since the elastic force (the repelling force or the force of returning to the original state) becomes relatively small around the vertex portion 531, it fits to the nose root or the nose bridge of a user 110 with a pressure of a predetermined value (for example, 15 mmHg) or less by its cushion property. The reinforcing members 1231 are preferably configured to be detachable. When medical staff attaches/detaches the reinforcing members in accordance with the shape of the face of the user, a mask with a high adhesion for any user can be implemented.

Figure 13:
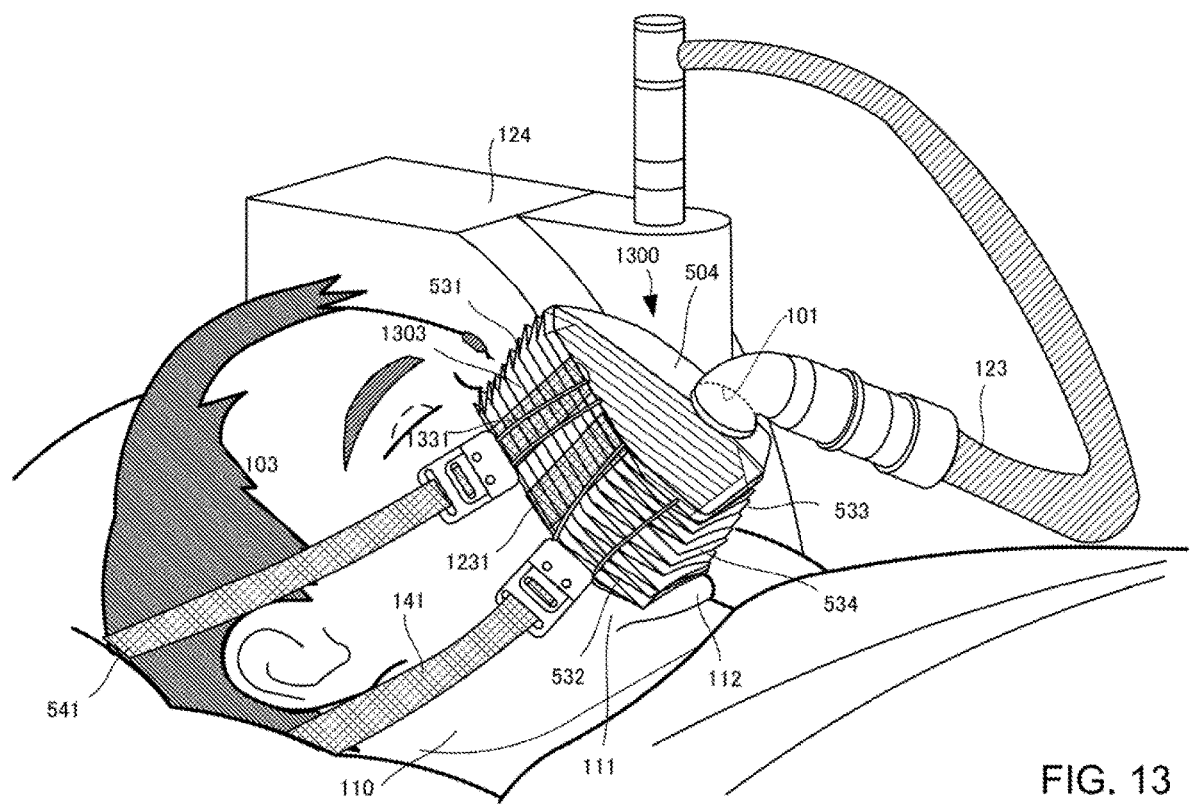
FIG. 13 is a view showing the use state of the mask according to the fourth example embodiment of the present invention.
Figure 14:
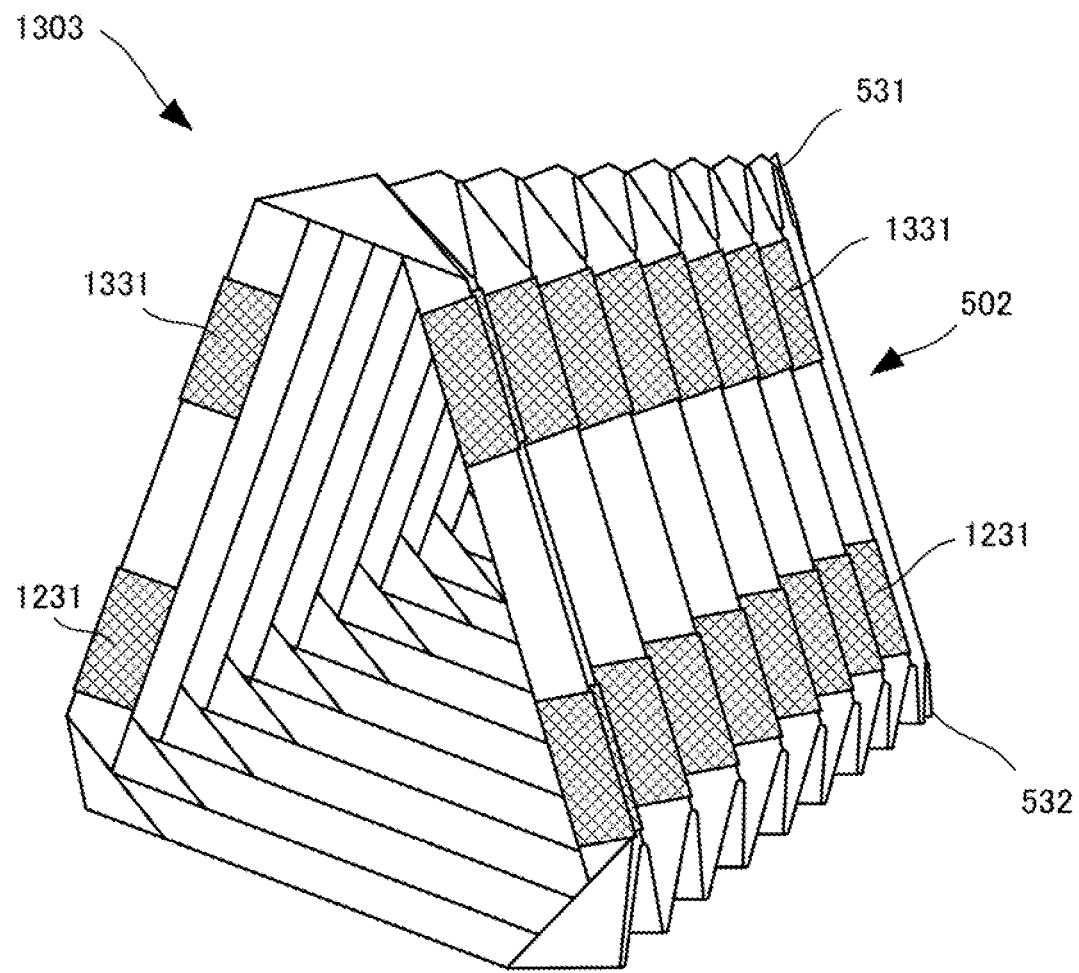
FIG. 14 is a view showing the shape of the bellows portion of the mask according to the fourth example embodiment of the present invention.

If the cheeks 111 of the user 110 are largely sunken, as shown in FIG. 13, a mask 1300 with additional reinforcing members 1331 may be formed. FIG. 14 is a perspective view showing a bellows portion 1303 extracted from the mask 1300, which is a perspective view viewed from the side of an opening portion 101. As shown in FIG. 14, each of the reinforcing members 1231 and 1331 is a plate-shaped member such as a cardboard adhered in the direction from the opening portion 101 to an opening portion 502 on the outer peripheral surface of the bellows portion 1303, and is mountain- and valley-folded along the bellows portion 1303.

However, the reinforcing member 1231 is not limited to this, and can have any configuration if a has a function of changing the elastic coefficient of the bellows depending on a place. For example, a spring configured to physically expand the two ends of the bellows portion may be attached. Alternatively, a spray or a liquid coating may be applied to control the stiffness of the material. In addition, the thickness, the hardness, or the material is preferably changed depending on a part to change the elastic force of the bellows (the thickness is increased on the cheeks to increase the elastic force, and the elastic force is decreased on the nose or chin). The number of folds of the bellows portion may be changed between a portion that hits the nose of the user and portions that hit the cheeks. For example, the number of folds of the portion that hits the nose of the user may be made smaller than the number of folds of the portions that hit the cheeks.

As described above, since the elastic force (the repelling force or the reproducing force) changes between the portion that hits the nose root of the user 110 and the portions that hit the cheeks, the bellows portion 1203 or 1303 can contact the nose root or the nose bridge at a relatively small pressure and contact the cheeks at a sufficient pressure. Since the nose root or the nose bridge is harder than the cheeks, pressure ulcers readily occur upon receiving the pressure from the mask. However, according to the mask 1200 or 1300 of this example embodiment, it is possible to very effectively avoid such pressure ulcers.

Figure 15:
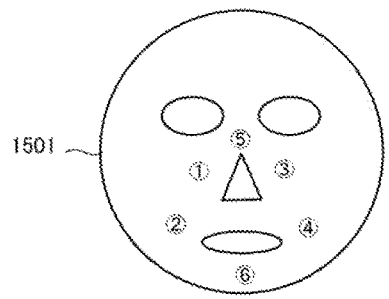
FIG. 15 is a view showing an example of the mask according to the fourth example embodiment of the present invention.

FIG. 15 shows a result of specifically conducting experiments. Pressure sensors were arranged at six points of a face 1501 of a user, the mask 1300 was attached, a mechanical ventilator was connected, and a contact pressure at each point was measured while sending oxygen (CPAP 10 cm H2O, Leak 40 L/min). The result is shown in a table 1502. The minimum value of the contact pressure was 4.5 mmHg, and the maximum value was 8 mmHg. The standard deviation was 1.5. As compared to a conventional product (Vivo50 available from Breas was used as an mechanical ventilator, and Simplus Masks available from Fisher & Paykel was used as a mask), both the maximum value of the contact pressure and the standard deviation are ½ or less, and the mask contacts the skin at a suitable and even contact pressure, as can be seen. That is, the numerical values show that according to this example embodiment, the attaching feeling for the user improves.

Other Example Embodiments

Figure 16:
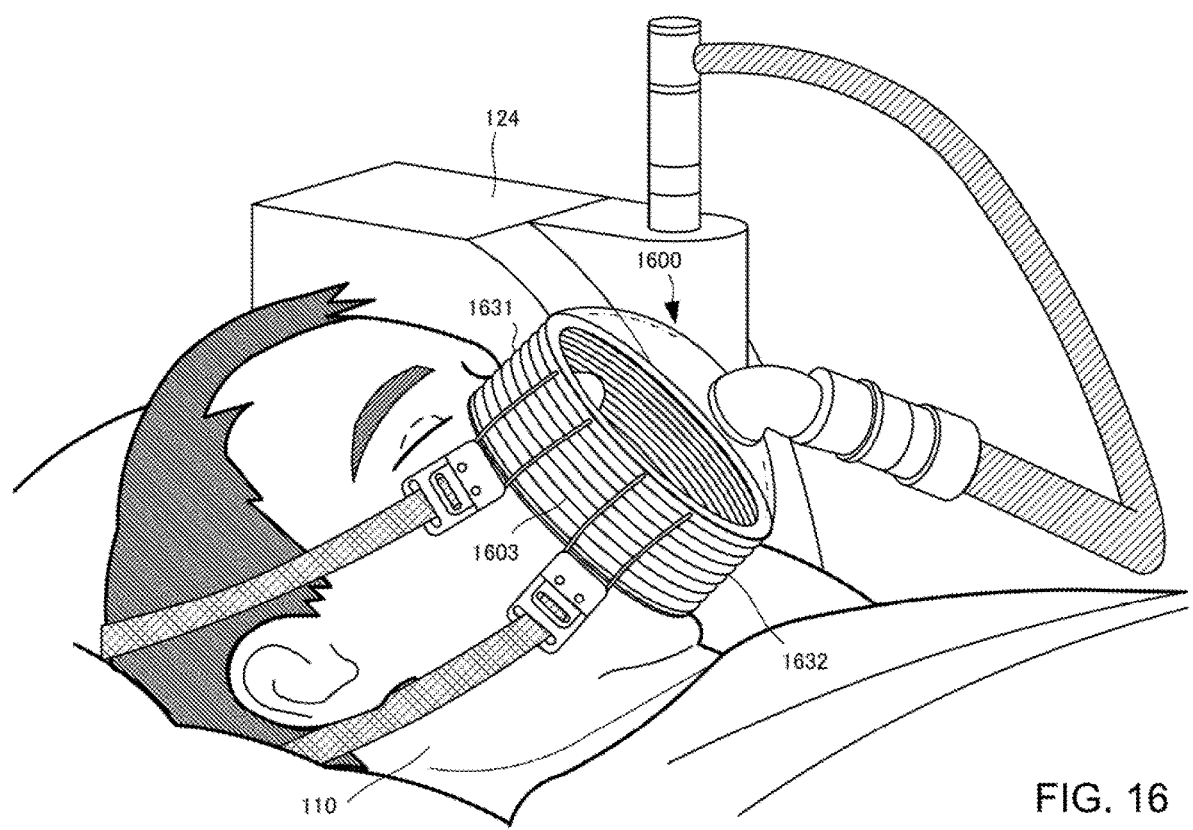
FIG. 16 is a view showing the use state of a mask according to another example embodiment of the present invention.
Figure 17:
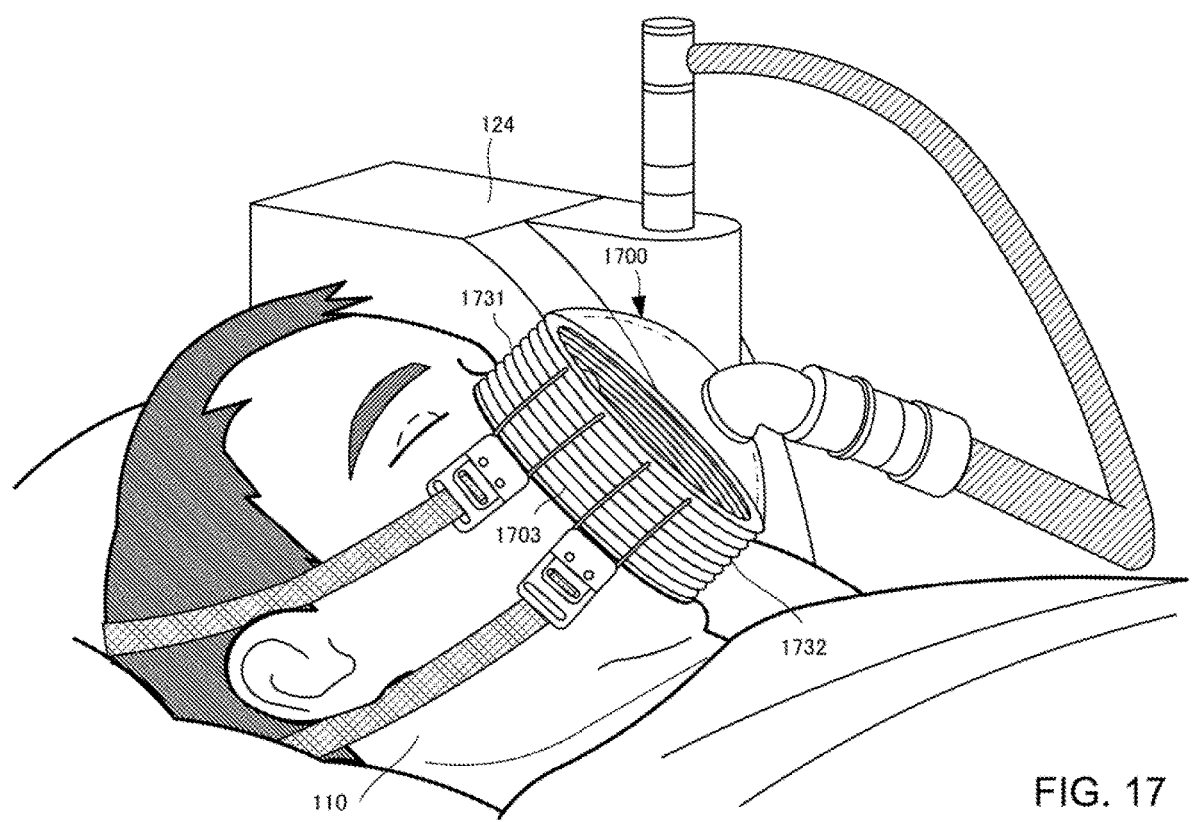
FIG. 17 is a view showing the use state of a mask according to still other example embodiment of the present invention.
Figure 18:
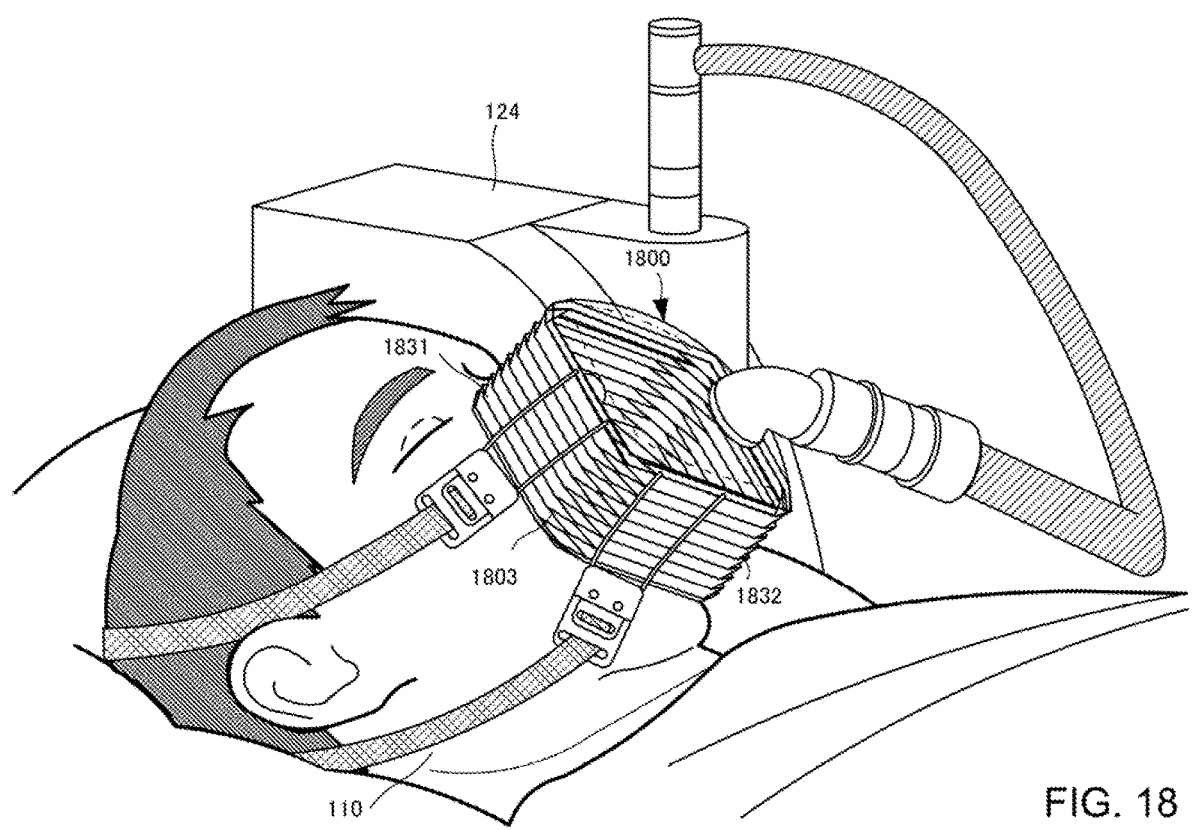
FIG. 18 is a view showing the use state of a mask according to still other example embodiment of the present invention.

Masks 1600, 1700, and 1800 according to other example embodiments of the present invention will be described with reference to FIGS. 16 to 18. FIGS. 16, 17, and 18 are views for explaining the use states of the masks 1600, 1700, and 1800.

The mask 1600 is different from the above-described example embodiments in that when viewed from the from of a user 110, a bellows portion 1603 has a circular shape having, as a diameter, a line that connects a portion 1631 abutting against the nose root or the nose bridge of the user 110 and a portion 1632 abutting against a chin 112. The rest of the components and operations is the same as in the second example embodiment. Hence, the same reference numerals denote the same components and operations, and a detailed description thereof will be omitted.

The mask 1700 is different from the above-described example embodiments in that when viewed from the front of a user 110, a bellows portion 1703 has an elliptical shape having, as a long axis, a line that connects a portion 1731 abutting against the nose root or the nose bridge of the user 110 and a portion 1732 abutting against a chin 112. The rest of the components and operations is the same as in the second example embodiment. Hence, the same reference numerals denote the same components and operations, and a detailed description thereof will be omitted.

The mask 1800 is different from the above-described example embodiments in that when viewed from the front of a user 110, a bellows portion 1803 has a rhombic shape having, as a diagonal line, a line that connects a portion 1831 abutting against the nose root or the nose bridge of the user 110 and a portion 1832 abutting against a chin 112. The rest of the components and operations is the same as in the second example embodiment. Hence, the same reference numerals denote the same components and operations, and a detailed description thereof will be omitted.

In addition, the bellows portion of the mask 1800 may have a rounded isosceles triangular shape, an equilateral triangular shape, a trapezoidal shape, a pentagonal shape, a hexagonal shape, other polygonal shapes, or a teardrop shape, or a combination thereof when viewed from the front of the user.

Other Example Embodiments

While the invention has been particularly shown and described with reference to example embodiments thereof, the invention is not limited to these example embodiments. It will be understood by those of ordinary skill in the art that various changes in form and details may be made therein without departing from the spirit and scope of the present invention as defined by the claims. A system or apparatus including any combination of the individual features included in the respective example embodiments may be incorporated in the scope of the present invention.

The invention claimed is:

1. A mask for a mechanical ventilator, comprising:
a first opening portion that takes in inspired air from the mechanical ventilator;
a second opening portion that has an edge configured to abut against a skin of a user to send the inspired air to at least one of a nose and a mouth of the user;
a bellows portion that is formed on at least a part of the edge of said second opening portion, forms a tubular space for temporarily storing the inspired air and expired air of the user between said first opening portion and said second opening portion, and includes a plurality of folds formed in a direction almost orthogonal to an axial direction of the tubular space and folded by a force of pressing from said first opening portion to said second opening portion, wherein the bellows portion is configured to contact the skin of a face of the user and to deform following a shape of the face of the user; wherein the plurality of folds comprising a mountain fold portion and a valley fold portion that is adjacent to the mountain fold portion, the valley fold portion comprising at least three straight sides, each straight side of the at least three straight sides of the valley fold portion meet one another to form at least three common vertices, the mountain fold portion comprising at least three mountain fold sides, each of the mountain fold side of the at least three mountain fold sides comprising two vertices having a peak formed between the two vertices of each of the mountain fold side, wherein an outer edge of each of the mountain fold side extends and descends from one of the two vertices of each of the mountain fold side to an end of a straight side of the at least three straight sides of the valley fold portion to form a common vertex of the at least three common vertices of the valley fold portion; and
a cover provided in a gap between an edge of said first opening portion and an edge of said bellows portion,
wherein said bellows portion includes the plurality of folds continuously formed from an outer periphery of said cover to the edge that is configured to abut against the skin of the user.

2. The mask for the mechanical ventilator according to claim 1, wherein when said cover deforms, said bellows portion deforms following the shape of the face of the user.

3. The mask according to claim 1, wherein if the mask is pressed against the face such that a pressure of not less than a predetermined value is applied to the skin of the user, said bellows portion deforms, thereby notifying the user or a person around the user that excessive pressing is being performed.

4. The mask according to claim 1, wherein said bellows portion changes a repelling force between a portion that is configured to hit a nose root of the user and a portion that is configured to hit a cheek of the user.

5. The mask according to claim 1, wherein said bellows portion includes a taper that is formed such that a cross section in a horizontal direction becomes narrow to a side of the mouth of the user.

6. The mask according to claim 1, wherein said bellows portion bends at a portion configured to abut against a chin of the user, thereby configured to deform following the shape of the face.

7. The mask according to claim 1, wherein said bellows portion changes a number of folds of a bellows between a portion configured to hit the nose and a portion configured to hit a cheek of the user.

8. The mask according to claim 1, wherein said bellows portion has one of an equilateral triangular shape, an isosceles triangular shape, a trapezoidal shape, a rhombic shape, a pentagonal shape, and a hexagonal shape when viewed from a front.

9. The mask according to claim 1, wherein an edge closest to said second opening portion is a mountain fold.

10. A mask comprising:
a first opening portion that takes in inspired air from a mechanical ventilator;
a second opening portion that has an edge configured to abut against a skin of a user to send the inspired air to at least one of a nose and a mouth of the user;
a bellows portion that is formed on at least a part of the edge of said second opening portion, forms a space for temporarily storing the inspired air and expired air of the user between said first opening portion and said second opening portion, and deforms following a shape of a face of the user; and
notifying means configured to, if the mask is pressed against the face such that a pressure of not less than a predetermined value is applied to the skin of the user, said bellows portion deforms, thereby notifying the user or a person around the user that excessive pressing is being performed, said notifying means being coloring of an outer peripheral portion of the bellows portion such that (1) a first symbol on the outer peripheral portion is darker and more visually recognizable than a second symbol on the outer peripheral portion in a first state in which excessive pressing is not being performed, and (2) the second symbol is darker and more visually recognizable than the first symbol in a second state in which excessive pressing is being performed, wherein the bellows portion is more expanded and less folded in the first state than in the second state.

11. The mask according to claim 10, wherein in a state in which said bellows portion is excessively folded, the edge of said first opening portion is configured to abut against a nose tip of the user.

12. The mask according to claim 10, wherein a part of said bellows portion configured to hit a nose root of the user has a different repelling force from a second part of said bellows portion configured to hit a cheek of the user.

13. A mask comprising:
a first opening portion that takes in inspired air from a mechanical ventilator;
a second opening portion that has an edge configured to abut against a skin of a user to send the inspired air to at least one of a nose and a mouth of the user; and
a bellows portion that is formed on at least a part of the edge of said second opening portion, forms a space for temporarily storing the inspired air and expired air of the user between said first opening portion and said second opening portion, and deforms following a shape of a face of the user,
a reinforcing member,
wherein the bellows portion comprising a left side portion, a right side portion, and a middle portion that is configured to hit a nose root of the user, the middle portion positioned between the left side portion and the right side portion, the reinforcing member is provided on a surface of the left side portion or the right portion and the reinforcing member is provided between a first vertex portion and a second vertex portion of said bellows portion, the reinforcing member being in contact with a plurality of folds of the bellows portion, the reinforcing member comprising folds having ridges and valleys, the ridges and valleys of the folds of the reinforcing member follow a contour of corresponding ridges and valleys of the plurality of folds of the bellows portion, one end of the reinforcing member being on an edge of the bellows portion that is in contact with the skin of the user, thereby changing a repelling force between the middle portion of the bellows portion that is configured to hit the nose root of the user and a portion of the bellows portion that is configured to hit a cheek of the user.

14. The mask according to claim 13, wherein if the mask is pressed against the face such that a pressure of not less than a predetermined value is applied to the skin of the user, said bellows portion deforms, thereby notifying the user or a person around the user that excessive pressing is being performed.

15. The mask according to claim 13, wherein said bellows portion has one of an equilateral triangular shape, an isosceles triangular shape, a trapezoidal shape, a rhombic shape, a pentagonal shape, a hexagonal shape, an elliptical shape, a circular shape, and a teardrop shape when viewed from a front.

* * * * *